US006063628A

United States Patent [19]
Loeb et al.

[11] Patent Number: 6,063,628
[45] Date of Patent: May 16, 2000

[54] INDUCTION OF VIRAL MUTATION BY INCORPORATION OF MISCODING RIBONUCLEOSIDE ANALOGS INTO VIRAL RNA

[75] Inventors: Lawrence A. Loeb, Bellevue; James I. Mullins, Seattle, both of Wash.

[73] Assignee: University of Washington, Seattle, Wash.

[21] Appl. No.: 08/958,065

[22] Filed: Oct. 27, 1997

Related U.S. Application Data

[60] Provisional application No. 60/029,404, Oct. 28, 1996, and provisional application No. 60/040,535, Feb. 27, 1997.

[51] Int. Cl.[7] ........................... C12N 15/00; C12N 15/85; C12P 19/34; C07H 21/02
[52] U.S. Cl. .................... 435/442; 435/91.3; 435/91.32; 435/235.1; 435/236; 435/325; 435/366; 435/372.3; 435/440; 435/441; 536/22.1; 536/23.1
[58] Field of Search .......................... 435/6, 91.3, 91.32, 435/91.33, 440, 441, 442, 235.1, 236, 325, 366, 372, 372.3; 536/22.1, 23.1; 514/44

[56] References Cited

U.S. PATENT DOCUMENTS

| 4,072,574 | 2/1978 | Loeb et al. | 435/6 |
| 5,512,431 | 4/1996 | Loeb et al. | 435/5 |

OTHER PUBLICATIONS

Halle, S., 5–Azacytidine as a Mutagen for Arboviruses, Journal of Virology, 2(10): 1228–1229, (Oct. 1968).
Pringle, C.R., Genetic Characteristics of Conditional Lethal Mutants of Vesicular Stomatitis Virus Induced by 5–Fluorouracil, 5–Azacytidine, and Ethyl Methane Sulfonate, Journal of Virology, 5(5):559–567, (May 1970).
Holland et al., Mutation Frequencies at Defined Single Codon Sites in Vesicular Somatitis Virus and Poliovirus Can Be Increased Only Slightly by Chemical Mutagenesis, Journal of Virology, 64(8): 3960–3962, (Aug. 1990).

Kim et al. A Screen in *Eschericia coli* for Nucleoside Analogs that Target Human Immunodeficiency Virus (HIV) Reverse Transcriptase: Coexpression of HIV Reverse Transcriptase and Herpes Simplex Virus Thymidine Kinase. J. Virol. 1995. vol. 69. No. 10. pp. 6563–6566.
Gait et al. Synthetic Ribonucleotide Analogs for RNA Structure–Function Studies. Nucleosides Nucleotides. 1995. vol. 14. No. 3–5, pp. 1133–1144.
Perelson, A. S., *Science* 271:1582 (1966).
Larder, B. A., *Science* 246:1155 (1989).
Larder, B.A., *J. Gen. Virol.* 75:951 (1994).
Ho, D., *Science* 272:1124 (1996).
Summers and Mason, *Cell* 29:403 (1982).
Beasley and Hwang, *Seminars in Liver Disease* 4:113 (1984).
Ehrlich, et al., *Virology* 186:619 (1992).
Zurcher, et al., *J. Gen. Virol.* 77:1745 (1996).
Gretch, et al., *Ann. Intern. Med.* 123:321 (1995).
Becker, *Virus–Genes* 9:33 (1994).
Horsnell, et al., *J. Gen. Virol.*, 76:2549 (1995).
Poonian et al., *J. Med. Chem.* 19:1017 (1976).
Srivastava et al., *J. Med. Chem.* 19:1020 (1976).
Velazquez et al., Int. Conf AIDS (Netherlands) Jul. 19–24 1992 8(2) pA57 (Abstract No. PoA 2324).
Tanaka et al.,*J. Synthetic Organic Chemistry*, Japan 49:1142 (1991).

*Primary Examiner*—John S. Brusca
*Assistant Examiner*—Mark L. Shibuya
*Attorney, Agent, or Firm*—Townsend and Townsend and Crew LLP

[57] ABSTRACT

The present invention is directed to the identification and use of ribonucleoside analogs to induce the mutation of an RNA virus, including HIV and HCV, or a virus which otherwise replicates through an RNA intermediate. The increase in the mutation rate of the virus results in reduced viability of progeny generations of the virus, thereby inhibiting viral replication. In addition to these methods and related compositions, the invention provides methods and combinatorial chemistry libraries for screening ribonucleoside analogs for mutagenic potential.

22 Claims, 4 Drawing Sheets

INDUCTION OF VIRAL MUTATION BY INCORPORATION OF MISCODING RIBONUCLEOSIDE ANALOGS INTO VIRAL RNA

This application claims the benefit of provisional applications, Ser. No. 60/029,404, filed Oct. 28, 1996, and Ser. No. 60/040,535, filed Feb. 27, 1997, which are herein incorporated by reference for all purposes.

BACKGROUND OF THE INVENTION

The present invention is directed to the identification and use of ribonucleoside analogs to induce the mutation of an RNA virus, including HIV and HCV, or a virus which otherwise replicates through an RNA intermediate.

RNA viral diseases are responsible for the vast majority of viral morbidity and mortality of viral diseases of mankind, including AIDS, hepatitis, rhinovirus infections of the respiratory tract, flu, measles, polio and others. Acquired Immune Deficiency Syndrome ("AIDS") is a fatal human disease that has recently grown in epidemic proportions. Current estimate is that there are approximately one million surviving infected individuals in the United States and tens of millions throughout the world. Epidemiological evidence indicates that this disease is caused by the human immunodeficiency viruses, HIV-1 or HIV-2.

HIV is particularly difficult to eradicate for several reasons, including that it permanently incorporates its genetic material into the genome of infected cells, it replicates (Perelson, A. S., *Science* 271:1582 (1966) and mutates (Larder, B. A., *Science* 246:1155 (1989) at an exceptionally high rate and thereby avoids immune inactivation, and it specifically infects and destroys the very immune system components most critical to controlling the infection. There is currently no effective vaccine for prevention of infection, and aside from the recent preliminary success for combination therapies involving protease inhibitors, few treatments of this fatal disease. Furthermore, the virus rapidly develops mutations conferring resistance against all chemotherapeutic agents tested to date.

All currently approved anti-AIDS drugs are designed to inhibit either the human immunodeficiency virus reverse transcriptase (HIV RT) or the virally encoded protease or a combination thereof. Chemicals directed against HIV RT are either deoxynucleoside analogs that terminate HIV DNA synthesis or non-nucleoside analogs that inhibit the reverse transcriptase (Larder, B. A., *J. Gen. Virol.* 75:951 (1994). The guiding concept of all current AIDS therapies is to prevent the further replication of the virus by directing drugs to interfere with the production or maturation of viral encoded proteins. Unfortunately, the therapeutic effectiveness of these drugs is generally rendered obsolete by the emergence of resistant viral mutations. It has been estimated that the mutation rate of HIV is one million times greater than the mutation rate of human cells. Recently, combinations of drugs have been shown to be more effective in reducing the viral load in individuals and it is hoped that this reduction in viral load will result in prolongation of life (Ho, D., *Science* 272:1125 (1996). It remains to be determined whether or not the reduction in circulating virus will prevent the development of drug resistant mutants in an infected individual. Furthermore, the rigors of the current treatment modalities that slow or prevent the appearance of protease inhibitor (PRI) resistant virus are so extreme that it is unlikely that they will be consistently adhered to, hence the spread of PRI resistant virus is expected to occur and increase over time, sharply curtailing expectations of drug efficacy. Moreover, the high mutation rate of HIV guarantees that while multiple therapies may be effective for the individual, the genetic makeup of the HIV in the infected population will change and HIV will become resistant to any widely used therapy.

There are a number of other chronic persistent diseases caused by RNA or DNA viruses that replicate through an RNA intermediate which are equally difficult to treat. Among the candidate human viral diseases are hepatitis B and C, T-cell human leukemia as well as other diseases. Important RNA viral diseases of animals include feline leukemia and immunodeficiency, *Visna maedi* of sheep, equine infectious anemia, caprine arthritis encephalitis and bovine leukemia. Even though the viruses that are associated with these diseases are replicated by an RNA dependent DNA polymerase, the RNA genomes are synthesized by the mammalian RNA polymerase.

Hepatitis B is caused by a DNA virus that replicates its genome through an RNA intermediate (Summers and Mason, *Cell* 29:4003 (1982). While an effective vaccine exists as a preventive there is no efficacious treatment for chronic persistent infection. Currently, it is estimated that 50 million individuals who harbor the virus are carriers and are chronically infected. Chronic infection with hepatitis B is associated with a 217-fold increase in primary hepatoma and invariably fatal cancer (Beasley and Hwang, *Seminars in Liver Disease* 4:113 (1984). Hairy cell leukemia is associated with HTLV-1 infection and is prevalent in Japan (Ehrlich, et al., *Virology* 186:619 (1992). The association of an RNA tumor virus with this human cancer could be predictive of a relation of RNA viruses with other human cancers but this remains to be established.

Finally, a number of common human diseases are caused by RNA viruses that are replicated by a viral encoded RNA replicase. Included in this group are influenza (Zurcher, et al., *J. Gen. Virol.* 77:1745 (1996), hepatitis C (Gretch, et al., *Ann. Intern. Med.* 123:321 (1995), dengue fever (Becker, *Virus-Genes* 9:33 (1994), and rhinovirus infections (Horsnell, et al., *J. Gen. Virol.*, 76:2549 (1995). Replication of these viruses by the viral RNA replicase is error prone and thus these viruses are likely to evolve rapidly and evade conventional drug or immunotherapies. Currently there is no effective therapy for these diseases. While vaccination against influenza can be effective, a new vaccine must be generated each year depending on the mutations that were fixed in the circulating strain in the previous year, a consequence of the rapid evolution of the viral genome. Current treatment of hepatitis C employs interferon, but it is seldom curative for the disease.

Thus, there exists a need for an effective prevention or amelioration of RNA virus mediated diseases. The present invention satisfies this need and provides related advantages as well.

SUMMARY OF THE INVENTION

The present invention provides a new strategy for inhibiting viral replication. In the methods of the invention, ribonucleoside analogs are used to dramatically increase the mutation rate of the virus. This increase in the mutation rate of the virus results in reduced viability of progeny generations of the virus, thereby inhibiting viral replication. In addition to these methods and related compositions, the invention provides methods and combinatorial chemistry libraries for screening ribonucleoside analogs for mutagenic potential. The methods provided herein run counter to current approaches for attacking RNA viruses. Where current methodologies are directed to thwarting or inhibiting viral enzymes and the incorporation of viral nucleic acid into host DNA, the present invention targets the role of cellular and viral RNA polymerases in the replication of the virus.

In many of the methods of the invention, the ribonucleoside analog is incorporated by an RNA polymerase into an RNA encoding a viral genomic nucleic acid. In a preferred embodiment, multiple RNA nucleoside analogs are administered to the virally infected cell.

Thus, in one class of embodiments, the invention provides methods of increasing the mutation rate of a virus by administering an RNA nucleoside analog to a virally infected cell. The cell can be in culture, or present in an animal such as a human patient. The analog is incorporated by an RNA polymerase into an RNA copy of a genomic nucleic acid encoding the virus, thereby inducing the virus to mutate.

In preferred embodiments, the RNA nucleoside analog could substitute for one or more of the naturally occurring ribonucleosides. A template dependent polymerase will incorporate the ribonucleoside opposite a complementary or non-complementary nucleoside in the template. Subsequent copying of the incorporated analog will result in mutations in the viral genome. This results in variability in template-dependent copies of the nucleic acid. Over time, accumulation of these induced variations (i.e., mutations) causes loss of viability in progeny viruses.

Ordinarily, the RNA nucleoside analog is incorporated by the RNA polymerase into the RNA copy of the genomic nucleic acid with an efficiency of at least about 0.1% that of a naturally occurring complementary nucleic acid. Thus, an error rate of about 1 in 1000 bases is induced. In comparison, typical polymerase error rates are on the order of 1 in 10,000 to 10,000,000 incorporated bases.

The RNA nucleoside or ribonucleoside will be an analog that will substitute for a naturally occurring ribonucleotide when incorporated by a polymerase into an RNA copy of a genomic nucleic acid encoding the virus of interest wherein the analog complements a second ribonucleotide and induces the virus to mutate. Typically the ribonucleoside analog will be either an analog of cytidine, uridine, adenosine or guanosine; analogs of cytidine and uridine being the most preferred. One class of preferred cytidine nucleoside analogs are selected from the group consisting of $N^4$-aminocytidine, $N^1$-methyl-$N^4$-aminocytidine, 3,$N^4$-ethenocytidine, 3-methylcytidine, 5-hydroxycytidine, $N^4$-dimethylcytidine, 5-(2-hydroxyethyl)cytidine, 5-chlorocytidine, 5-bromocytidine, $N^4$-methyl-$N^4$-aminocytidine, 5-aminocytidine, 5-nitrosocytidine, 5-(hydroxyalkyl)-cytidine, 5-(thioalkyl)-cytidine and cytidine glycol. A class of preferred uridine analogs includes 5-hydroxyuridine, 3-hydroxyethyluridine, 3-methyluridine, $O^2$-methyluridine, $O^2$-ethyluridine, 5-aminouridine, $O^4$-methyluridine, $O^4$-ethyluridine, $O^4$-isobutyluridine, $O^4$-alkyluridine, 5-nitrosouridine, 5-(hydroxyalkyl)-uridine, and 5-(thioalkyl)-uridine. A class of preferred adenosine analogs includes 1,$N^6$-ethenoadenosine, 3-methyladenosine, and $N^6$-methyladenosine. A class of preferred guanosine analogs includes 8-hydroxyguanosine, $O^6$-methylguanosine, $O^6$-ethylguanosine, $O^6$-isopropylguanosine, 3,$N^2$-ethenoguanosine, $O^6$-alkylguanosine, 8-oxo-guanosine, 2,$N^3$-ethenoguanosine, and 8-aminoguanosine. The nucleoside analog, however, may also be a compound that does not resemble the naturally occurring nucleotides, but will substitute for the natural nucleoside and result in mutation of the virus and can be developed and synthesized on the basis of modeling studies or other similar information. For example, see Bergstrom et al, *J. Chem. Soc. Perkin Trans.* (1994) 3029 for the production of comparable deoxynucleoside analogs.

Preferably, the RNA polymerase is a mammalian RNA polymerase II (pol II). Examples include human and murine pol II. optionally, the polymerase can be RNA polymerase III.

In one class of embodiments, viral particles comprising RNA nucleoside analogs are a feature of the invention. Replication of copies of these RNA nucleic acids in a cell can result in mutated viral nucleic acids incorporated into the cellular genome. The presence of such mutated viral nucleic acids provides an indication of the degree of success of the mutation and inhibition of the virus. The mutated RNA nucleic acids can also be used as probes to detect corresponding naturally occurring nucleic acids, e.g., in a northern blot, or, after translation into a corresponding DNA, by Southern blot. Similarly, the mutated viral particle can be used to detect antisera against the wild-type virus, e.g., in a western or ELISA assay on a biological sample.

The invention also provides a population of cells containing a highly variable population of replicated viral nucleic acids. This population of highly variable virus results from administering mutagenic nucleoside analogs to virally infected cells and increasing the mutation rate of the virus population. Thus, the highly variable population of viruses is an indicator that the mutation rate of the virus was increased by the administration of the nucleoside analogs. Measuring the variability of the population provides an assessment of the viability of the viral population. In turn, the viability of the viral population is a prognostic indicator for the health of the cell population. For example, low viability for an HIV population in a human patient corresponds to an improved outlook for the patient. In addition, the viral nucleic acids can also be used as probes to detect corresponding naturally occurring nucleic acids, e.g., in a Southern or northern blot, which is a useful diagnostic indicator for the presence of the wild-type virus.

In one embodiment, the invention provides a cell comprising a viral genomic nucleic acid, an RNA analog, a cellular mRNA analog and a viral genomic RNA analog. These are, e.g., cells which are being treated for a viral infection. These cells are useful for producing mutant viruses, which serve, e.g., as molecular decoys in subsequent cellular infections by the mutant viruses. The mutant viruses are also useful as diagnostic reagents for the detection of antisera against wild-type viruses, e.g., in an ELISA or western assay, or a Southern or northern blot. Because the mutant viruses have reduced viability, they are less pathogenic than wild-type viruses.

The viral genomic nucleic acid may be one that is integrated into the cellular genome. Examples of viruses which integrate their cellular genome include, but are not limited to, retroviruses. In one particularly preferred embodiment, the virus is HIV. Other preferred viruses include HIV-1, HIV-2, HTLV-1, HTLV-II, and SIV. Alternatively, the viral genome can be episomal. These include many human and animal pathogens such as flaviviruses such as dengue fever and yellow fever, filoviruses such as ebola virus, influenza viruses, parainfluenza viruses, including respiratory syncytial virus, measles, mumps, the picornaviruses, including the echoviruses, the coxsackieviruses, the polioviruses, the togaviruses, including encephalitis, coronoviruses, rubella, bunyaviruses, reoviruses, including rotaviruses, rhabdoviruses, arenaviruses such as lymphocytic choriomeningitis as well as other RNA viruses of man and animals. Retroviruses that can be targeted include the human T-cell leukemia (HTLV) viruses such as HTLV-1 and HTLV-2, adult T-cell leukemia (ATL), the human immunodeficiency viruses such as HIV-1 and HIV-2 and simian immunodeficiency virus (SIV).

Assays for detecting the mutagenic potential of a ribonucleoside analog are provided. In the assays, the ribonucleoside analog is incorporated into a viral RNA synthesized by a cellular or viral RNA polymerase, and a determination is made regarding whether the incorporation causes a mutation in a progeny virus. In certain embodiments, the virus is a retrovirus such as HIV-1, HIV-2, HTLV-1, or SIV, or an RNA virus such as hepatitis A, hepatitis B, hepatitis C or dengue fever virus.

In another class of assays of the invention, methods of screening for ribonucleoside analogs which are incorporated by a cellular or viral RNA polymerase are provided. In the assay, the RNA polymerase is incubated with the ribonucleoside analog in the presence of a nucleic acid template. The incorporation of the ribonucleoside analog into a nucleic acid polymer is then detected. Optionally, naturally occurring (i.e., G, A, U, and/or C) nucleotides are also incorporated into the nucleic acid polymer. The method optionally comprises comparing the rate of incorporation of the ribonucleoside analog and any naturally occurring ribonucleoside in the assay into the RNA polymer.

Pharmaceutical compositions are provided. The compositions have a therapeutically effective dose of a mis-pairing RNA nucleoside analog and a pharmaceutically acceptable carrier. Preferred RNA nucleoside analogs are those specified above. Preferred compounds are suitable for oral or parenteral administration.

Methods of increasing the mutation rate of a virus in an animal are provided. In the methods, a therapeutically effective dose of an RNA nucleoside analog is administered to the animal. For example, the animal may be a human patient infected with a virus selected from the group consisting of HIV-1, HIV-2, HTLV-1, hepatitis A, hepatitis B, hepatitis C, dengue fever virus. In preferred embodiments, the RNA nucleoside analog is incorporated by a polymerase present in virally infected cells of the animal into an RNA copy of a genomic nucleic acid of the virus with an efficiency range at least about 0.1% that of a naturally occurring complementary nucleic acid. This method provides treatment for, inter alia, AIDS, hepatitis B, hepatitis C and T-cell leukemia. Treatment of non-human infections are also provided, including, but not limited to, feline leukemia virus infections, feline immunodeficiency virus infections, and vesicular stomatitis virus infections.

Libraries of RNA nucleoside and nucleotide analogs are provided. Each nucleoside analog comprises a random chemical substituent covalently linked to a group selected from the group consisting of uridine, cytidine, guanosine, adenosine, $N^4$-aminocytidine, $N^1$-methyl-$N^4$-aminocytidine, 3,$N^4$-ethenocytidine, 3-methylcytidine, 5-hydroxycytidine, $N^4$-dimethylcytidine, 5-(2-hydroxyethyl)-cytidine, 5-chlorocytidine, 5-bromocytidine, $N^4$-methyl-$N^4$-aminocytidine, 5-aminocytidine, 5-nitrosocytidine, 5-(hydroxyalkyl)-cytidine, 5-(thioalkyl)-cytidine and cytidine glycol, 5-hydroxyuridine, 3-hydroxyethyluridine, 3-methyluridine, $O^2$-methyluridine, $O^2$-ethyluridine, 5-aminouridine, $O^4$-methyluridine, $O^4$-ethyluridine, $O^4$-isobutyluridine, $O^4$-alkyluridine, 5-nitrosouridine, 5-(hydroxyalkyl)-uridine, and 5-(thioalkyl)-uridine, 1,$N^6$-ethenoadenosine, 3-methyladenosine, and $N^6$-methyladenosine, 8-hydroxyguanosine, $O^6$-methylguanosine, $O^6$-ethylguanosine, $O^6$-isopropylguanosine, 3,$N^2$-ethenoguanosine, $O^6$-alkylguanosine, 8-oxo-guanosine, 2,$N^3$-ethenoguanosine, and 8-aminoguanosine and derivatives thereof. Optionally, a plurality of the nucleotide analogs are polymerized into a nucleic acid. The library optionally includes a cellular RNA polymerase for incorporating nucleoside analogs. The library typically includes between about 5 and 1,000,000 different analogs.

Methods of identifying mutagenic ribonucleoside analogs are provided. In the methods, a plurality of ribonucleoside analogs are first provided to a reaction mixture which includes a cellular or viral RNA polymerase. The RNA polymerase permits incorporation of the nucleotide analog. The ribonucleoside polymer is typically isolated and the chemical composition of ribonucleoside analogs which are incorporated into the ribonucleoside polymer determined. Methods of isolation include electrophoresis, column chromatography, affinity beads and the like. The composition of the isolated polymer is determined, e.g., by hydrolyzing the ribonucleoside polymer and assessing the substituents of the polymer, e.g., by mass spectroscopy or NMR.

Methods of making mutagenic ribonucleoside or ribonucleotide analogs are provided. In the methods, a ribonucleotide or ribonucleoside analog selected from the group consisting of guanosine, uridine, cytidine, adenosine, $N^4$-aminocytidine, $N^1$-methyl-$N^4$-aminocytidine, 3,$N^4$-ethenocytidine, 3-methylcytidine, 5-hydroxycytidine, $N^4$-dimethylcytidine, 5-(2-hydroxyethyl)cytidine, 5-chlorocytidine, 5-bromocytidine, $N^4$-methyl-$N^4$-aminocytidine, 5-aminocytidine, 5-nitrosocytidine, 5-(hydroxyalkyl)-cytidine, 5-(thioalkyl)-cytidine and cytidine glycol, 5-hydroxyuridine, 3-hydroxyethyluridine, 3-methyluridine, $O^2$-methyluridine, $O^2$-ethyluridine, 5-aminouridine, $O^4$-methyluridine, $O^4$-ethyluridine, $O^4$-isobutyluridine, $O^4$-alkyluridine, 5-nitrosouridine, 5-(hydroxyalkyl)-uridine, and 5-(thioalkyl)-uridine, 1,$N^6$-ethenoadenosine, 3-methyladenosine, and $N^6$-methyladenosine, 8-hydroxyguanosine, $O^6$-methylguanosine, $O^6$-ethylguanosine, $O^6$-isopropylguanosine, 3,$N^2$-ethenoguanosine, $O^6$-alkylguanosine, 8-oxo-guanosine, 2,$N^3$-ethenoguanosine, and 8-aminoguanosine is chemically modified, e.g., by treatment with oxygen free radicals. The resulting chemically modified ribonucleoside analog is tested to determine whether it is incorporated by a RNA polymerase into an RNA molecule, and the mutagenic potential of the chemically modified analog is measured.

Also included within the invention is a method of increasing the mutation rate of a virus, comprising administering a free base selected from the group comprising adenine, cytosine, guanine, uracil and thymine to a virally infected cell, wherein the base is incorporated by a polymerase into an RNA or DNA copy of a genomic nucleic acid encoding the virus. The base replaces a first natural occurring nucleotide having a first complementary nucleotide, but the base also complements a second nucleotide which is other than the first nucleotide, thereby inducing the virus to mutate.

Kits for practicing the methods of the invention and optionally including the compositions of the invention are also provided. For example, a kit comprising a container and one or more of the following components: a control mutagenic RNA analog, a test mutagenic RNA analog, an RNA polymerase, reagents for detecting incorporation of the RNA analog by the RNA polymerase are provided. Optionally, the kits include instructions to facilitate practice of the methods of the invention. For example, in one kit, instructions in the use of the kit components for detecting the mutagenic potential of the test mutagenic analog as compared to the control mutagenic RNA analog are provided.

DEFINITIONS

Unless otherwise defined herein, the terms used throughout the specification shall have the meaning commonly associated with them by those practicing in the field of virology and molecular biology. The following definitions are provided to better explain terms used in connection with the invention:

A "ribonucleoside" contains a heterocyclic nitrogenous base, either adenine (A), guanine (G), cytosine (C), or uracil (U) joined to a ribose; upon the addition of a phosphate group the compound becomes a ribonucleotide. Nucleotides are phosphate esters of nucleosides. The polymerized nucleotides deoxyribonucleic acid (DNA) and ribonucleic acid (RNA) store the genetic information which ultimately controls a cell's or organism's interaction with its environment. Ribonucleosides are the nucleosides common in RNA which makes up the bulk of nucleic acids in all cells. The nucleosides of RNA are connected together via phosphate units attached to the 3' position of one pentose and the 5' position of the next pentose.

The four "naturally occurring nucleotides" in RNA contain adenine, guanine, uracil or cytosine. Nucleotides which are complementary to one another are those that tend to form complementary hydrogen bonds between them and, specifically, the natural complement to A is U, the natural complement to U is A, the natural complement to C is G and the natural complement to G is C.

A "nucleic acid" is a deoxyribonucleotide or ribonucleotide polymer in either single- or double-stranded form, and unless otherwise limited, encompasses analogs of natural nucleotides.

A "ribonucleoside analog" as used herein is defined in more detail below and includes analogs of ribonucleosides and the triphosphates thereof. These monomeric units are nucleoside analogs (or "nucleotide" analogs if the monomer is considered with reference to phosphorylation). For instance, structural groups are optionally added to the ribose or base of a nucleoside for incorporation into an oligonucleotide, such as a methyl or allyl group at the 2'-O position on the ribose, or a fluoro group which substitutes for the 2'-O group, or a bromo group on the ribonucleoside base. The phosphodiester linkage, or "sugar-phosphate backbone" of the oligonucleotide analog is substituted or modified, for instance with methyl phosphonates or O-methyl phosphates. However, a nucleoside which is a naturally occurring nucleoside (i.e., those comprising DNA or RNA), with the exception of a protecting group on the end of the nucleoside, such as a protecting group used during standard nucleic acid synthesis is not considered a nucleoside analog for purposes of this invention. Ribonucleoside analogs are further defined below.

A "genomic nucleic acid" is a nucleic acid polymer which is homologous to a nucleic acid which encodes a naturally occurring nucleic acid polymer (RNA or DNA) packaged by a viral particle. Typically, the packaged nucleic acid encodes some or all of the components necessary for viral replication. The genomic nucleic acid optionally includes nucleotide analogs. Nucleic acids are homologous when they are derived from a nucleic acid with a common sequence (an "ancestral" nucleic acid) by natural or artificial modification of the ancestral nucleic acid. Retroviral genomic nucleic acids optionally encode an RNA which is competent to be packaged by a retroviral particle. Such nucleic acids can be constructed by recombinantly combining a packaging site with a nucleic acid of choice.

A "nucleic acid reagent" utilized in standard nucleic acid synthesis typically carries a protected phosphate on the 3' hydroxyl of the ribose. Thus, nucleic acid reagents are referred to as nucleotides, nucleotide reagents, nucleoside reagents, nucleoside phosphates, nucleoside-3'-phosphates, nucleoside phosphoramidites, phosphoramidites, nucleoside phosphonates, phosphonates and the like. It is generally understood that nucleotide reagents carry a protected phosphate group in order to form a phosphodiester linkage.

A "protecting group" as used herein, refers to any of the groups which are designed to block one reactive site in a molecule while a chemical reaction is carried out at another reactive site. The protecting groups used herein can be any of those groups described, e.g., in Greene, et al., *Protective Groups In Organic Chemistry*, 2nd Ed., John Wiley & Sons, New York, N.Y., 1991, which is incorporated herein by reference.

A "virally infected cell" is a cell transduced with a viral nucleic acid. The nucleic acid is optionally incorporated into the cellular genome, or is optionally episomal.

The "mutation rate" of a virus or nucleic acid refers to the number of changes which occur upon copying the nucleic acid, e.g., by a polymerase. Typically, this is measured over time, i.e., the number of alterations which occur during rounds of copying or generations of virus.

An "RNA polymerase" refers to an enzyme that produces a polyribonucleotide sequence, complementary to a pre-existing template polynucleotide (DNA or RNA). The RNA polymerase may be either an RNA viral polymerase or replicase or RNA cellular polymerase. A "cellular polymerase" is a polymerase derived from a cell. The cell may be prokaryotic or eukaryotic. The polymerase is typically an RNA polymerase such as Pol II or Pol III. Pol II enzymes are most preferred. A "mammalian polymerase II" is an RNA polymerase II derived from a mammal. The polymerase is optionally naturally occurring, or artificially (e.g., recombinantly) produced. A "human polymerase II" is an RNA polymerase II derived from a human. The polymerase is optionally naturally occurring, or artificially (e.g., recombinantly) produced. A "murine polymerase II" is an RNA polymerase II derived from a mouse. The polymerase is optionally naturally occurring, or artificially (e.g., recombinantly) produced.

A "cell culture" is a population of cells residing outside of an animal. These cells are optionally primary cells isolated from a cell bank, animal, or blood bank, or secondary cells cultured from one of these sources, or long-lived artificially maintained in vitro cultures which are widely available.

A "progressive loss of viability" refers to a measurable reduction in the replicative or infective ability of a population of viruses over time.

An "HIV particle" is a retroviral particle substantially encoded by HIV. The presence of non-HIV viral or cellular components in the particle is a common result of the replication process of HIV which typically includes budding from a cellular membrane. In certain applications, retroviral particles are deliberately "pseudotyped" by co-expressing viral proteins from more than one virus (often HIV and VSV) to expand the host range of the resulting retroviral particle. The presence or absence of non-HIV components in an HIV particle does not change the essential nature of the particle, i.e., the particle is still produced as a primary product of HIV replication.

A "highly variable population of homologous replicated nucleic acids" is a population of homologous nucleic acids which have been derived by natural or artificial replication from a related population of nucleic acids, or, alternatively, a clonal population of a particular nucleic acid, such as the nucleic acids found from an infection by a virus. The homologous nucleic acids often have at least 1% difference in comparison of their nucleic acids, typically at least 5%, generally at least 10%, sometimes at least 20%, occasionally at least 30%, and sometimes at least 40% or more. It will be appreciated that natural replication of a viral nucleic acid results in typically less than 0.1% variability in progeny viruses. Thus, an average difference of 1% or more in a nucleic acid population as described above is highly variable compared to a natural population of replicated virus in a particular cell population.

Where the methods discussed below require sequence alignment, such methods of alignment of sequences for comparison are well known in the art. Optimal alignment of sequences for comparison may be conducted by the local homology algorithm of Smith and Waterman (1981) *Adv. Appl. Math.* 2:482; by the homology alignment algorithm of Needleman and Wunsch (1970) *J. Mol. Biol.* 48:443; by the search for similarity method of Pearson and Lipman (1988) *Proc. Natl. Acad. Sci. USA* 85:2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene*, 73:237–244 and Higgins and Sharp (1989) *CABIOS* 5:151–153; Corpet, et al., (1988) *Nucleic Acids Research* 16, 10881–90; Huang, et al., (1992) *Computer Applications in the Biosciences* 8, 155–65, and Pearson, et al., (1994) *Methods in Molecular Biology* 24, 307–31. Typically, the alignments are visually inspected and refined manually after computer-aided adjustment.

A "library" of nucleoside analogs is a mixture or array of more than one analog. The mixture or array is optionally a liquid or present on a solid-phase substrate. Methods of placing assay components into arrays and performing parallel analysis of the arrayed components is available. See, Fodor et al., (1991) *Science*, 251:767–777; Lipshutz et al., (1995) *BioTechniques* 19(3):442–447; Fodor et al., (1993) *Nature* 364:555–556; and Medlin (1995) *Environmental Health Perspectives* 244–246. Mixtures are optionally assayed in multi-well plates such as standard 96 well microtiter plates. In either liquid mixtures or solid phase assays, the libraries can comprise a number of RNA analogs, typically from about 1 to about 10,000,000, generally from about 5 to about 1,000,000.

DETAILED DESCRIPTION

Figure 1A:
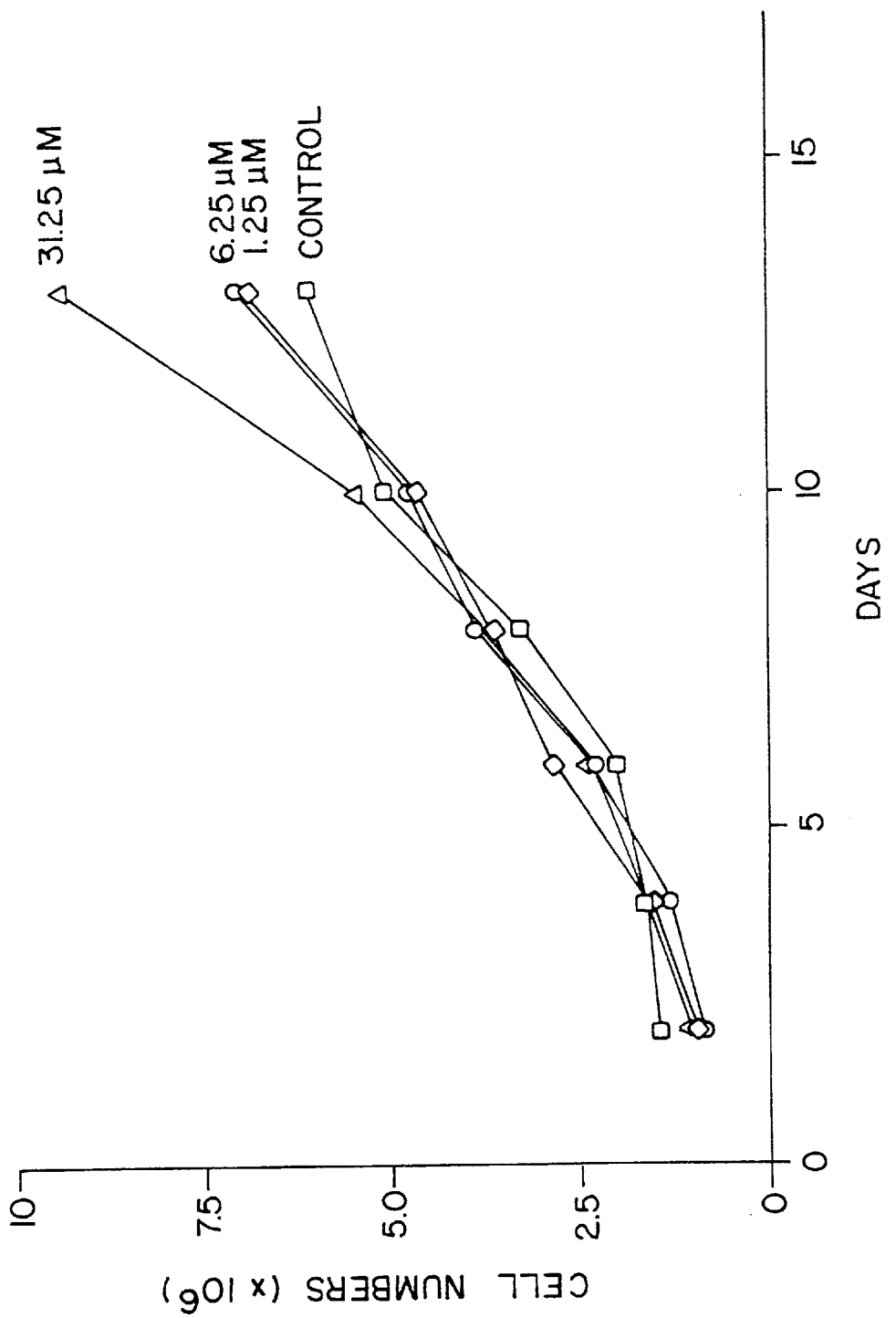
FIGS. 1A and 1B illustrate a toxicity assay of ribonucleoside analogs 5-bromocytidine (FIG. 1A) and 5-hydroxyuridine (FIG. 1B) on CEMx174 cells.

The invention is directed to a new method of inducing viral mutagenesis which is useful in cell culture as well as in therapy. This method is significantly advantageous in that it is one useful against RNA viruses in general and DNA viruses that have an RNA intermediate. It is particularly compelling for use against retroviruses because, unlike other therapy approaches, its efficacy is not thwarted by the mutagenicity of the virus itself. Our methods, in part, exploit the inherent differences in the fate of viral RNA and of host cell messenger RNA (Coffin, J., *Science* 267:483 (1995). The methods of the invention utilize miscoding ribonucleosides that are incorporated into both viral encoded and cellular encoded mRNAs by RNA polymerase thereby causing miscoding in progeny copies of the genomic virus.

The methods of the invention are particularly advantageous when used to target retroviruses or other viruses otherwise replicated by an RNA intermediate. In human cells, the genetic material is DNA, it is replicated during each cellular division by DNA polymerases that catalyze the polymerization of deoxyribonucleotide triphosphates. The information that DNA contains is transcribed into messenger RNA by RNA polymerase which polymerizes ribonucleoside triphosphates. The newly synthesized messenger RNA guides the synthesis of proteins that carry out cellular functions. When retroviruses infect a cell, the same cellular RNA polymerase synthesizes the cell's messenger RNA and the viral RNA. With respect to the methods described herein for the treatment of RNA virus-mediated diseases, the major difference is that the cellular messenger RNA is used for protein synthesis and has a short half life. In contrast, the viral RNA is packaged into virions and used to infect new cells. As a result alterations in the viral RNA and not the cellular RNA is passed to subsequent generations.

The viruses which may be targeted by the methods described herein include RNA viruses as well as DNA viruses that replicate via an RNA intermediate. For example, the methods will be useful to target RNA viruses such as hepatitis viruses A, C, D, E and G, flaviviruses such as dengue fever and yellow fever, filoviruses such as ebola virus, influenza viruses, parainfluenza viruses, including respiratory syncytial virus, measles, mumps, the picornaviruses, including the rhinoviruses, the echoviruses, the coxsackieviruses, the polioviruses, the togaviruses (including encephalitis-causing togaviruses), coronaviruses, rubella, bunyaviruses, including hantaviruses, reoviruses, including rotaviruses, rhabdoviruses, arenaviruses such as lymphocytic choriomeningitis as well as other RNA viruses of man and animals. The preferred RNA viruses include hepatitis C, dengue fever, influenza, and respiratory synctial virus. Retroviruses that can be targeted include the human T-cell leukemia (HTLV) viruses such as HTLV-1 and HTLV-2, adult T-cell leukemia (ATL), the human immunodeficiency viruses such as HIV-1 and HIV-2, simian immunodeficiency virus (SIV), feline leukemia virus (FeLV) and feline immunodeficiency virus (FIV).

Hepatitis C is a virus particularly well-suited for the methods of this invention. It has been tentatively classified in a separate genus, Hepacivirus of the Flavivirus family. It is about 9.5 kb in size and has extensive genotypic diversity. Replication of the virus in cultured cells tends to be inefficient. Chimpanzees serve as the animal model of choice for testing. Infectious cDNA clones have been derived. The genome organization for the virus is:

5'UTR (340 nt)–ORF (9000 nt)-3'UTR (200–300 nt), where

"UTR"=untranslated region,

"ORF"=open reading frame,

"nt"=nucleotides.

The open reading frame is constructed as follows:
C-E1-E2-NS2-NS3-NS4-NS5,
where:
- c=RNA binding nucleocapsid
- E1/E2=envelope glycoproteins
- NS2=$Zn_2$ and metalloproteinase with NS3
- NS3=serine protease, helicase
- NS4=unknown
- NS5=N terminus is unknown, but the C terminal is RNA dependent RNA polymerase.

The flu virus, influenza, can lead to croup in children and more serious bacterial pneumonia, cardiac or neurologic involvement. It is an orthomyxovirus that replicates in the nucleus. The virus (such as influenza A, ATCC VR-98) may be cultured on Madin Darby canine kidney cells or chick embryo cells.

Respiratory syncytial virus is the most frequent cause of fatal acute respiratory infection in infants and young children. About 25–33% of such cases are serious, requiring hospitalization. It is a paramyxovirus about 15 kb in size and is very contagious. Strain ATCC VR-955 can be grown in Hep2 cells and ATCC VR-1040 can be grown in Vero cells.

DNA viruses that replicate via an RNA intermediate include hepatitis B. Further information regarding viral diseases and their replication can be found in White and Fenner, *Medical Virology* 4th ed. Academic Press (1994) and in *Principles and Practice of Clinical Virology*, ed. Zuckerman, Banatvala and Pattison, John Wiley and Sons (1994).

The methods of the invention utilize nucleoside analogs that miscode at high frequency and are incorporated into genomic copies of the viral nucleic acid by an RNA polymerase present in the cell or by a viral RNA polymerase. Even though the host cell messenger RNA will likely also contain the nucleoside analogs and will mispair with tRNAs to yield cellular proteins with altered amino acid sequences it is a transitory phenomena. Miscoding by messenger RNA is not significantly detrimental to host cell functions; these altered mRNA have a short life span in cells and are not incorporated into the genome of progeny cells. As a result errors in coding by cellular mRNA are transitory and are not passed onto subsequent cellular generations. These toxic effects are limited to each cell division and do not accumulate.

In contrast, the viral RNA containing the altered nucleosides is encapsulated within the progeny virions. In the infected cells, the viral RNA, in the case of retroviruses, is reverse transcribed and the DNA product is integrated into the cell's genome or the viral nucleic acid is directly copied to produce new viral RNAs. Since these analogs miscode at high frequencies, the DNA product of the reverse transcription reaction or the RNA product of a viral RNA polymerase contains noncomplementary nucleotides. As a result, the mutations in the viral genome are perpetuated and accumulated with each viral replication cycle. In contrast, the cellular RNA is not reverse transcribed into DNA or replicated into mutant RNAs and thus does not cause mutations in the host genome. With each cycle of viral replication there ensues a chain like increase in the number of mutations in the viral genome. Eventually the number of mutations in each viral genome is so large that no active virally encoded proteins are produced. This method provides a unique method to exceed the error threshold for significant viral viability, such as that of HIV, without causing significant toxicity to host cells.

RNA viruses frequently mutate at exceptionally high rates. As a result, there is no single nucleotide sequence that defines a specific virus, and instead the RNA virus exists as a quasipecies characterized by variations in sequence surrounding a common founder or a "consensus" sequence. Many of the virions are already inactive since they harbor many mutations that produce defective proteins. A small increase in the frequency of mutations caused by the incorporation of nucleotide analogs would lead to many more errors and the production of non-infective virions. In the case of HIV, the frequency of errors in the genome is about $10^{-3}$ to $10^{-4}$ and as a result viral replication may operate near the threshold for the production of active viral progeny. In the case of hepatitis B, the compacted genome encodes a multiplicity of proteins and thus even a small increase in errors might not be tolerated. As a result therapy based on enhanced mutagenesis can be even more effective in eliminating the viral population.

In the case of retroviruses or other RNA viruses, the fact that the modified nucleotides are incorporated by the host cell enzymes and only cause mutations during reverse transcription or cytoplasmic RNA replication protects this protocol from the development of mutations in viral genes that render them resistant to nucleoside analogs. Mutations are introduced by the host cell RNA polymerase and not by an encoded viral enzyme. The methods of this invention are therefore in part unique in that they likely avoid the emergence of viral resistance, especially in the case of HIV that employs cellular RNA polymerase II for transcription of the viral genome. Mutations in the human genome that might render RNA polymerase II resistant to specific analogs would be rare since mutations in human cells occur at a very low frequency (DeMars, R., and Held, K. R., *Humangenetik*. 16:87–110 (1972), which is due to an exquisite mutation repair process not found in viruses. The methods of the invention do not use mutagenic deoxyribonucleotides that are incorporated into cellular DNA. Ribonucleotides incorporated into RNA that might render the RNA polymerase II resistant to the nucleotide analogs would not likely be propagated in subsequent cellular generations since there is no role for reverse transcription of cellular mRNAs leading to the generation of functional human genes (Temin, H. M., *Cancer Res*. 48:1697 (1988). The multiple rounds of viral replication that occur during the course of viral infection would be the driving force for the accumulation of mutations by the incorporated ribonucleoside analogs.

As noted above, the methods of the invention are counter-intuitive to the current rationale for the choice of nucleoside analogs against the viral reverse transcriptase. Instead of selecting analogs that target viral encoded enzymes, the methods described herein utilize ribonucleoside analogs that are incorporated by the host cell's enzymes. These analogs are incorporated into both the viral RNA and the host cell messenger RNA during transcription by RNA polymerase. The viral RNA containing the analogs are packaged into virions that infect new host cells. Without wishing to be bound by theory, it is believed that when the RNA is reverse transcribed or replicated in the newly infected cells it introduces non-complementary nucleotides into the viral nucleic acid. With each viral replication cycle there would ensue an augmentation of incorrect nucleotides throughout the viral genome. Mutations occurring in required genes result in mutated proteins with diminished functions. The production of viable viruses is progressively less with each round of viral replication. Furthermore, the presence of non-viable mutant viral genomes offers the possibility of curing the host cell genome of integrated viral copies (in the case of HIV infection) by homologous recombination or eventual natural clearance of circulating target cells.

The methods of increasing the mutation rate of a virus herein use RNA nucleoside analogs which are incorporated by an RNA polymerase into an RNA copy of a genomic nucleic acid encoding the virus, where the analog replaces a first natural occurring nucleotide having a first complementary nucleotide and wherein the analog complements a second nucleotide which is other than the first nucleotide, thereby causing incorrect base pairing and inducing the virus to mutate.

Preferred nucleoside analogs of the present invention can be incorporated and extended by a polymerase. Generally, such analogs have phosphodiester linkages allowing them to be extended by the polymerase molecule after their incorporation into RNA. Thus, unlike certain viral inhibitors which cause chain termination (e.g., analogs lacking a 3'-hydroxyl group), the preferred analogs of the present invention are non-chain-terminating analogs that generally do not result in the termination of RNA synthesis upon their incorporation. Instead, they are preferably error-inducing analogs, which can be incorporated into an RNA product but which effectively alter the base-pairing properties at the position of their incorporation, thereby causing the introduction of errors in the RNA sequence at the site of incorporation.

Determination of parameters concerning the incorporation of altered nucleotides by a cellular RNA polymerase such as, human RNA polymerase II and viral polymerases/ replicates or the phosphorylation of ribonucleoside analogs by cellular kinase, is made by methods analogous to those used for incorporation of deoxynucleoside triphosphates by DNA polymerases (Boosalis, et al., *J. Biol. Chem.* 262:14689–14698 (1987). In selected situations direct determination of the frequency of mutations that are introduced into the viral genome (Ji and Loeb, *Virol.*, 199:323–330 (1994) can be made.

The RNA nucleoside analog is incorporated by a cellular polymerase or viral polymerase into the RNA copy of the genomic nucleic acid with an efficiency of at least about 0.1%, preferably at least about 5%, and most preferably equal to that of a naturally occurring complementary nucleic acid when compared in equal amounts in an in vitro assay. Thus, an error rate of about 1 in 1000 bases or more would be sufficient to enhance mutagenesis of the virus. The ability of the ribonucleoside analog to cause incorrect base pairing may be determined by testing and examining the frequency and nature of mutations produced by the incorporation of an analog into RNA. It has been reported, for example, that the mutation rates in lytic RNA viruses (such as influenza A) are higher than in DNA viruses, at about 300-fold times higher, Drake, *PNAS, USA* 90:4171–4175 (1993). Retroviruses, however, apparently normally mutate at an average rate about an order of magnitude lower than lytic RNA viruses. Id.

For example, in the case of HIV, the viral RNA or the incorporated HIV DNA is copied by reverse transcriptase and then DNA polymerase using a PCR reaction with complementary primers and all four deoxynucleoside triphosphates. The region of the genome copied corresponds to a 600 nucleotide segment in the reverse transcriptase gene. The copied DNA or RNA after 70 rounds of PCR is treated with restriction enzymes that cleave the primer sequences, and ligated into a plasmid. After transfection of *E. coli*, individual clones are obtained and the amplified segment within the plasmid is sequenced. Mutations within this region are determined by computer aided analysis, comparing the individual sequences with control viral sequences obtained by parallel culturing of the same virus in the absence of the RNA analog. For each nucleotide, determinations are carried out after ten sequential rounds of viral passage or at the point of extinction for viral detection. Analogous procedures would be effective for other viruses of interest and would be readily apparent to those of skill in the art.

Incorporation of an analog by a cellular RNA polymerase, by reverse transcriptase (or other viral enzyme) or by DNA polymerase may be compared directly, or separately and the separate test results subsequently compared. A comparison of incorporation of analogs among the polymerases of interest can be carried out using a modification of the "minus" sequencing gel assay for nucleotide incorporation. A 5'-$^{32}$P-labeled primer is extended in a reaction containing three of the four ribonucleoside triphosphates and an analog in the triphosphate form. The template can be either RNA or DNA, as appropriate. Elongation of the primer past the template nucleotide that is complementary to the nucleotide that is omitted from the reaction will depend and be proportional to the incorporation of the analog. The amount of incorporation of the analog is calculated as a function of the percent of oligonucleotide that is extended on the sequencing gel from one position to the next. Incorporation is determined by autoradiography followed by either densitometry or cutting out each of the bands and counting radioactivity by liquid scintillation spectroscopy.

Assays for detecting the mutagenic potential of a ribonucleoside analog can be similarly conducted. In the assays, the ribonucleoside analog is incorporated into a viral RNA synthesized by an RNA polymerase, and determining whether the incorporation causes a mutation in a progeny virus, by any of the means discussed above.

When a ribonucleoside analog of the invention is administered to virally infected cells, either in vitro or in vivo, a population of cells is produced comprising a highly variable population of replicated homologous viral nucleic acids. This population of highly variable cells results from administering mutagenic nucleoside analogs to virally infected cells and increasing the mutation rate of the virus population. Thus, the highly variable population of viruses is an indicator that the mutation rate of the virus was increased by the administration of the nucleoside analogs. Measuring the variability of the population provides an assessment of the viability of the viral population. In turn, the viability of the viral population is a prognostic indicator for the health of the cell population. For example, low viability for an HIV population in a human patient corresponds to an improved outlook for the patient.

Preferably, the mutagenic ribonucleoside analog of choice will be water soluble and have the ability to rapidly enter the target cells. Though generally less desirable, a lipid soluble analog will also have use, particularly where it is necessary to penetrate the blood-brain barrier. The ribonucleoside analog will be phosphorylated by cellular kinases and incorporated into RNA. The analog of choice will also be more effective as a mutagen than as a chain terminator for copying by the host cell RNA polymerase or by an RNA replicase.

The ribonucleoside analog used in the present invention is typically an analog of cytidine, uridine, adenosine or guanosine. Each of such ribonucleosides are understood to be composed of a purine or pyrimidine moiety and a ribose moiety. As with the naturally-occurring ribonucleosides, the sugar portion of the monomers will have hydroxyl groups at the 2'-, 3'- and 5'-positions of the ribose. As used herein, the term "ribonucleoside analog" is also meant to include the mono-, di- or triphosphates of the above nucleosides. Each of the analogs will be capable of being incorporated and extended into RNA and will produce oligomers which will cause incorrect base pairing. The ability of an analog to cause incorrect base pairing may be determined by testing as described above. For the purpose herein, the definition of "ribonucleoside analog" includes the proviso that ribavirin (See, Poonian et al., J.Med. Chem. 19:1017 (1976) and 5-halo analogs of 1-β-D-ribofuranosylimidazole-4-carboxamide (See, Srivastava et al. J. Med. Chem. 19:1020 (1976)) are specifically excluded from the definition and the proviso that 2',5'-bis-O-silylated-3'-spiro-substituted (TSAO) adenine, hypoxanthine, $N^1$-alkyl-hypoxanthine or xanthine (See, Velazquez et al. Int. Conf AIDS (Netherlands) Jul. 19–24, 1992 8(2) pA57 (Abstract No. PoA 2324); 1-[(2-hydroxyethoxy)methyl]-6-phenylthiothymine (HEPT) (See, Tanaka et al. J.Synthetic Organic Chemistry, Japan 49:1142 (1991); and any nucleotide analog that is incorporated and extended at high efficiency by reverse transcriptase of HIV (all as defined in U.S. Pat. No. 5,512,431) are specifically excluded from the definition when the targeted virus is HIV.

The cytidine analogs used in the present invention will be, for example, $N^4$-aminocytidine, $N^1$-methyl-$N^4$-aminocytidine, ethenocytidine, 3-methylcytidine, $N^4$-dimethylcytidine, 5-hydroxycytidine, 5-chlorocytidine, 5-bromocytidine and cytidine glycol. Some of the analogs can be purchased from commercial suppliers such as Sigma Chemical Co. (St. Louis, Mo., USA) or can be synthesized by methods known to those of skill in the art. For the above compounds, $N^4$-aminocytidine, ethenocytidine, and 3-methylcytidine are commercially available. Cytidine glycol and 5-hydroxycytidine can be synthesized by methods similar to those described in U.S. Pat. No. 5,512,431, previously incorporated by reference. Accordingly, cytidine glycol can be prepared based on the published procedure for thymidine (Basu, et al., *Proc. Natl. Acad. Sci.* 86:7677–7681 (1989)), involving an osmium tetroxide oxidation of thymidine. In a similar manner, treatment of cytidine with osmium tetroxide in an aqueous buffer at room temperature provides 5,6-dihydro-5, 6-dihydroxycytidine which can be purified on HPLC. 5-hydroxycytidine can be prepared via treatment of cytidine with $Br_2$ in water (see, Eaton, et al., *Biochim. Biophys. Acta* 319:281–287 (1973).

$N^4$-aminocytidine may be prepared according to the procedure of Negishi et al. (*Nucleic Acid Res.* 11:5223 (1983)) using commercially available cytidine as a starting material. $N^4$-aminocytidine has been shown to be mutagenic in vitro and in the Ames Assay (Negishi, et al., Biochemistry 24:7273, 1985). The ribonucleoside triphosphate derivative is synthesized by treatment of CTP with hydrazine and sodium bisulfite.

$N^1$-methyl-$N^4$-aminocytidine and $N^4$-methyl-$N^4$-aminocytidine may be prepared in accordance with A. Nomura, K. Negishi, H. Hayatsu, *Nucleic Acids Research* 13:8893 (1985). The above compounds are formed simultaneously on treatment of cytidine with monomethyl hydrazine in the presence of bisulfite. The desired products are readily purified by RP-18 HPLC.

$N^4$-dimethycytidine may be prepared in accordance with *Journal of the American Chemical Society*, 83:4755 (1961). Benzoyl-protected uridine is thiated by phosphorous pentasulfide in pyridine to the 4-thio analog. Treatment of the 4-thio-tribenzoate uridine with dimethylamine affords the desired $N^4$-dimethylcytidine product.

5-hydroxycytidine and 5-bromocytidine may be prepared as follows: Cytidine was used as the precursor following a variation of the preparation by Visser, D. W. (1968) in *Synthetic Procedures in Nucleic Acid Chemistry* (Zurbach, W. W. & Tipson, R. S., Eds.) Vol. I, pp. 428–430, Interscience Publisher, New York). Cytidine is treated with aqueous bromide at room temperature, followed by addition of pyridine and subsequent dehydration of the diol intermediate which affords the desired 5-hydroxycytidine nucleoside. 5-bromocytidine is obtained simultaneously from the dehydration of the monobromo-hydroxyl intermediate.

Examples of uridine derivatives which are useful in the present invention include, for example, 5-hydroxyuracil, 3-hydroxyethyluridine, 3-methyluridine, $O^2$-methyluridine, $O^2$-ethyluridine, $O^4$-methyluridine, $O^4$-ethyluridine, $O^4$-isobutyluridine, and the like. Among this group of derivatives, 3-methyluridine is commercially available. 3-hydroxyethyluridine can be prepared by treating uridine with ethylene oxide as described for 3-hydroxyethyldeoxyuridine (see, Bhanot, et al., *J. Biol. Chem.* 47:30056 (1994)). Similarly, the $O^2$-alkyl and $O^4$-alkyl derivatives of uridine can be prepared by suitable modifications of methods used to prepare $O^2$-alkyl and $O^4$-alkyl thymidines. In particular, U.S. Pat. No. 5,512,431 describes the preparation of $O^4$-methylthymidine, $O^4$-ethylthymidine, $O^4$-isopropylthymidine and $O^4$-isobutylthymidine (see also the published procedures of Xu, et al., *Nucleic Acids Res.* 18:4061–4065 (1990)). In each of these syntheses, the 3'- and 5'-hydroxyl groups of the deoxyribose portion are first protected as their t-butyldimethylsilyl ethers. In a similar fashion, the three hydroxyl groups (2'-, 3'- and 5'-) of the ribose portion of uridine are protected either in a single step or in subsequent protection steps. For example, protection of both of the 2'- and 3'-hydroxyl groups can be accomplished via formation of a suitable acetonide. Alternative groups for the protection of the adjacent diols can be found in Greene, et al., PROTECTIVE GROUPS IN ORGANIC SYNTHESIS, 2nd ed., John Wiley & Sons, New York, 1991, Chap. 2, pages 118–142, incorporated herein by reference. After protection of the three ribose hydroxyl groups, the introduction of an alkyl ether to the C4 position of the pyrimidine ring can continue as described in the above-cited patent. Preparation of the $O^2$-alkyluridines will typically follow the procedures which have been outlined for the preparation of $O^2$-alkylthymidines (see, for example, Singer, *Biochemistry* 28:1478–1483 (1989), and references cited therein).

$N^3$-(2-hydroxyethyl)uridine is prepared by treating uridine with ethylene oxide as described for the preparation of 3-hydroxyethyldeoxyuridine (Bhanot, O. S., et al., *J. Biol. Chem.* 47: 30056 (1994)). The deoxynucleoside triphosphate derivative has been shown to be mutagenic in in vitro assays (Bhanot, O. S., et al., *J. Biol. Chem.* 47: 30056 (1994)).

$O^4$-methyluridine and $O^4$-alkyluridines may be prepared in accordance with *Nucleic Acids Research* 18:4061 (1990). $O^4$-methyluridine is synthesized from the 4-triazolo derivative of uridine. Upon substitution of the 4-triazolo group with methoxide, the desired $O^4$-methyluridine can be obtained. In addition, additional $O^4$-alkylated uridines can be obtained by substituting other alkoxides for the methoxide used in this example.

5-nitrosouridine and 5-nitrosocytidine may be prepared in accordance with *Advanced Organic Chemistry of Nucleic Acids*, Z. Ahabarova and A. Bogdanov, Editors, p. 40, VCH, New York. An hydroxyl group protected uridine or cytidine treated with $HNO_3$ and sulfuric acid followed by deprotection affords the corresponding 5-nitrosouridine or 5-nitrosocytidine nucleosides.

5-aminouridine and 5-aminocytidine may be prepared in accordance with *Advanced Organic Chemistry of Nucleic*

*Acids*, Z. Ahabarova and A. Bogdanov, Editors, p. 40, VCH Publishing Co. The 5-amino derivatives of uridine or cytidine are obtained from the reduction of the corresponding 5-nitrosouridine or 5-nitrosocytidine nucleosides.

5-(hydroxyalkyl)-uridine, 5-(thioalkyl)-uridine, 5-(hydroxyalkyl)-cytidine, and 5-(thioalkyl)-cytidine may be prepared in accordance with S. Sun, et al., *Journal of Organic Chemistry* 1996 61:5708 (1996). Hilbert-Johnson glycosylation reaction of peracylated glucose with pyrimidines and isomerization of alpha-ureidomethylene lactones forms 5-(hydroxyalkyl)-uridines. Thiolactones provide the corresponding 5-(thioalkyl)-uridines. These nucleosides are converted directly to their corresponding cytidine derivatives via ring opening of the 4-triazole intermediate.

Adenosine derivatives which are useful in the present invention include, for example, 1,$N^6$-ethenoadenosine, 3-methyladenosine, and $N^6$-methyladenosine. 1,$N^6$-ethenoadenosine and $N^6$-methyladenosine are commercially available from Sigma Chemical Co.

Guanosine derivatives which are useful in the present invention include, for example, 8-hydroxyguanosine, $O^6$-methylguanosine, $O^6$-ethylguanosine, $O^6$-isopropylguanosine, 3,$N^2$-ethenoguanosine, $O^6$-alkylguanosine, 8-oxo-guanosine, 2,$N^3$-ethenoguanosine, and 8-aminoguanosine. Each of these derivatives can be prepared using methods similar to those used for the corresponding deoxyguanosine compounds in U.S. Pat. No. 5,512,431. In particular, an additional protection step (and deprotection step) will typically be required to mask the 2'-hydroxyl group of the guanosine derivatives for those reactions in which an unprotected hydroxyl group could interfere with the desired reaction. Other reactions are modified simply by use of a different starting material. For example, 3,$N_2$-ethenoguanosine can be prepared according to the procedure of Kusmicrek, et al., *Chem. Res. Tox.* 5:634–638 (1992) by substituting guanosine for 2'-deoxyguanosine. Similarly, 8-aminodeoxyguanosine can be prepared from guanosine using the procedure of Long, et al., *J. Org. Chem.* 32:2751–2756 (1967), for the related 2'-deoxyguanosine.

One of skill in the art will understand that other ribonucleoside derivatives can be prepared and utilized in the methods of the present invention, such as, for example, halogenated derivatives. Other modifications can be made to the above ribonucleoside analogs using radical reactions. Examples of suitable radical reactions include those involving oxygen free radicals, bromine free radicals, and the like. When bromine free radicals are used to generate brominated ribonucleoside derivatives, the analogs can be further converted to chlorinated or fluorinated derivatives via displacement of the bromide with the desired halide.

For use in the present inventive methods, the ribonucleoside derivatives above will preferably be prepared as their mono-, di- or triphosphates. The phosphorylation of the ribonucleoside analogs is typically carried out by enzymatic methods, chemical methods or combinations of enzymatic and chemical methods. Enzymatic phosphorylation can be carried out using a crude source of wheat shoot extract as a source of phosphotransferase activity (see Giziewicz, et al., *Acta. Biocim. Pol.* 22:87–98 (1975); and Sugar, IN MOLECULAR ASPECTS OF CHEMOTHERAPY, Springer-Verlag, 1991, pp. 240–270). Phosphorylation can also be carried out using Herpes virus thymidine kinase or mutants thereof as described by Black, et al., *Biochemistry* 32:11618–11626 (1993). Herpes thymidine kinase has a wide substrate specificity and phosphorylates a wide variety of nucleoside analogs. Purification of the resultant monophosphates can be accomplished using HPLC.

Further conversion of the monophosphate derivatives to the triphosphates will typically use chemical methods such as those provided in Hoard, et al., *J. Am. Chem. Soc.* 87:1785–1788 (1965), incorporated herein by reference.

As is known in the art, nucleosides, ribonucleosides and analogs thereof can be prepared as racemic mixtures or as enantio-specific compositions which have a prevalence of one or another enantiomeric species (typically greater than about 70% prevalence, more preferably greater than about 90%, still more preferably greater than about 98%). For example, one can obtain or synthesize enantio-specific nucleoside analogs or ribonucleoside analogs that are predominantly in an unnatural or L-enantiomeric configuration (e.g., by incorporating an L-ribose in place of a D-ribose). Enantio-specific nucleoside compositions can be employed in the context of the present invention to further optimize activity and minimize toxicity. By way of illustration, for a racemic mixture exhibiting activity in the context of the present invention, one of the enantio-specific compositions thereof would typically exhibit greater activity and/or greater specificity (and thus fewer potential side effects at any given concentration) than the other. Enantio-specific compositions of such an analog can therefore be employed to optimize efficacy and/or specificity.

Enantio-specific analogs (and/or other structural variations) can also be employed to influence the intracellular localization of analogs to be used in the context of the present invention. In particular, an enantio-specific or other variant analog can be more efficiently processed by cellular machinery involved in the uptake or intracellular localization of such analogs. For example, one can employ analogs which are preferentially taken up by (and/or localized in the cytosol of) a targeted mammalian cell. Again, by way of illustration, for a racemic mixture exhibiting activity in the context of the present invention, one of the enantio-specific compositions thereof would typically exhibit greater cellular uptake (and/or greater partitioning to the cytosol) than the other. Such structural variations would also be expected to influence the efficiency at which an analog is processed by an enzyme—such as cellular kinases capable of converting a nucleoside to a nucleoside phosphate prior to incorporation, or cellular degradative enzymes such as phosphatases; thereby enabling the isolation of compositions exhibiting greater activity and/or stability.

In addition to the above ribonucleoside analogs and ribonucleoside analog triphosphates, the present invention will utilize certain derivatives which are prepared using combinatorial synthesis methods. For example, mixtures of the monomers described above can be protected using standard synthetic methods, then subjected to one or more chemical transformations such as dehydrations, light induced bond scission or isomerization, oxidations, reductions, alkylations, acylations and the like. The resulting mixtures of ribonucleoside analogs can then be deprotected and evaluated for the ability of each monomer to substitute for the complementary nucleoside triphosphate during synthesis by RNA polymerase II or one of the virally encoded RNA replicases using chain elongation reactions. The ribonucleoside polymer is typically isolated and the chemical composition of ribonucleoside analogs which are incorporated into the ribonucleoside polymer determined. Methods of isolation include electrophoresis, column chromatography, affinity beads and the like. The composition of the isolated polymer is determined, e.g., by hydrolyzing the ribonucleoside polymer and assessing the substituents of the polymer, e.g., by mass spectroscopy or NMR. For the purposes of the present invention, the libraries will typically contain of from about five to about one million chemical species. Preferably, the libraries will contain from about 100 to about 10,000 chemical species.

The ribonucleoside analogs of the invention will preferably be those that are incorporated and extended efficiently into RNA by a cellular RNA polymerase and cause incorrect base pairing. It is further preferred that such ribonucleoside analogs not be such that they can be incorporated by a DNA polymerase into DNA molecule or by a reverse transcriptase directly into a DNA molecule. Finally, it is further preferred that the ribonucleoside analogs not be strong inhibitors of polymerase activity.

Similarly and related to the ribonucleoside analogs, the free bases themselves, guanine, cytidine, uracil, thymine, and adenine can be used in place of ribonucleoside analogs in the methods described herein to induce mutagenesis of a DNA or RNA virus.

Kits for practicing the methods of the invention and optionally including the compositions of the invention are also provided. For example, a kit comprising a container and one or more of the following components: a control mutagenic RNA analog, a test mutagenic RNA analog, an RNA polymerase, reagents for detecting incorporation of the RNA analog by the RNA polymerase are provided. Optionally, the kits include instructions to facilitate practice of the methods of the invention. For example, in one kit, instructions in the use of the kit components for detecting the mutagenic potential of the test mutagenic analog as compared to the control mutagenic RNA analog are provided.

Administration of Ribonucleoside Analogs for Treatment of Viral Diseases.

Methods of increasing the mutation rate of mutation of a virus in an animal are provided. In the methods, a therapeutically effective dose of a mutagenic RNA nucleoside analog is administered to the animal. For example, the animal may be a human patient infected with a virus selected from the group consisting of the hepatitis viruses A, B, C, D, E and G, flaviviruses such as dengue fever and yellow fever, filoviruses such as ebola virus, influenza viruses, parainfluenza viruses, including respiratory syncytial virus, measles, mumps, the picornaviruses, including the rhinoviruses, the echoviruses, the coxsackieviruses, the polioviruses, the togaviruses, including encephalitis, corono viruses, rubella, bunyaviruses, including hantaviruses, reoviruses, including rotaviruses, rhabdoviruses, arenaviruses such as lymphocytic choriomeningitis, the human T-cell leukemia (HTLV) viruses such as HTLV-1 and HTLV-2, adult T-cell leukemia (ATL), the human immunodeficiency viruses such as HIV-1 and HIV-2 and simian immunodeficiency virus (SIV).

Preferred analogs for therapeutic applications include $N^4$-aminocytidine, $N^1$-methyl-$N^4$-aminocytidine, 3,$N^4$-ethenocytidine, 3-methylcytidine, 5-hydroxycytidine, $N^4$-dimethylcytidine, 5-(2-hydroxyethyl)-cytidine, 5-chlorocytidine, 5-bromocytidine, $N^4$-methyl-$N^4$-aminocytidine, 5-aminocytidine, 5-nitrosocytidine, 5-(hydroxyalkyl)-cytidine, 5-(thioalkyl)-cytidine and cytidine glycol, 5-hydroxyuridine, 3-hydroxyethyluridine, 3-methyluridine, $O^2$-methyluridine, $O^2$-ethyluridine, 5-aminouridine, $O^4$-methyluridine, $O^4$-ethyluridine, $O^4$-isobutyluridine, $O^4$-alkyluridine, 5-nitrosouridine, 5-(hydroxyalkyl)-uridine, and 5-(thioalkyl)-uridine, 1,$N^6$-ethenoadenosine, 3-methyladenosine, and $N^6$-methyladenosine, 8-hydroxyguanosine, $O^6$-methylguanosine, $O^6$-ethylguanosine, $O^6$-isopropylguanosine, 3,$N^2$-ethenoguanosine, $O^6$-alkylguanosine, 8-oxo-guanosine, 2,$N^3$-ethenoguanosine, and 8-aminoguanosine and derivatives. In preferred embodiments, the RNA nucleoside analog is incorporated by a polymerase present in virally infected cells of the animal into an RNA copy of a genomic nucleic acid of the virus with an efficiency at least about 0.1% that of a naturally occurring complementary nucleic acid. The ribonucleoside analogs discussed above can be incorporated into a pharmaceutically acceptable carrier for administration to a human or other mammal for treatment of an RNA viral infection or infection of a virus that replicates via an RNA intermediate as described above. The analogs can be administered singly or in multiples of two or more, either together in one dosage or in alternative dosages.

The antiviral compositions are preferably administered to human patients via oral, intravenous or parenteral administrations and other systemic forms, though other forms may be appropriate depending upon the primary sites of infection. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity and the like.

A therapeutically effective amount of a compound is that which results in a measurable decrease of infection or viral titer or which otherwise provides subjective relief of viral symptom(s) or an objectively identifiable improvement as noted by the clinician or other qualified observer.

The dosage of compound used in accordance with the invention will vary depending on the age, weight, and clinical condition of the recipient patient, the location and extent of the infection and the experience and judgment of the clinician or practitioner administering the therapy. For example, the dosage of a ribonucleoside analog as described herein can range from about 5 milligrams per kilogram (mg/kg) of body weight per day to about 250 mg/kg of body weight per day, preferably in the range of about 7.5 to 100 mg/kg of body weight per day and most preferably in the range of about 10 to about 40 mg/kg of body weight per day.

A preferred dose of the ribonucleoside analogs are administered to achieve peak plasma concentrations of the compound from about 1 to about 1000 $\mu$M, preferably about 5 to about 100 $\mu$M, most preferably about 7.5 to about 50 $\mu$M. This may be achieved, for example, by the intravenous injection of a sterile 0.1 to 5% solution of the administered ingredients in saline as a bolus containing about 1 to about 100 mg/kg of the active analog. Desirable blood levels may be maintained by a continuous or intermittent infusions adjusted accordingly. Preferably, the dosage is repeated daily until either a therapeutic result is achieved or until side effects warrant discontinuation of therapy.

It is further advantageous to administer the above ribonucleoside analogs together in combination with a drug that reduces the concentration of the natural occurring nucleotide which is being replaced by the ribonucleoside analog. Preferably, these additional drugs would be administered together in the same vehicle. One could administer drugs that interfere with the intermediary metabolism necessary for the synthesis of natural ribonucleotides. Chemical analysis could be used to verify that one reduces the concentration of the natural nucleoside that is homologous to the nucleotide analog being administered.

All patents, publications, and patent applications cited herein are incorporated herein by reference. The following examples are provided for illustrative purposes only and are not to be construed as limiting the invention in any way.

EXAMPLES

1. Modification of Ribonucleoside Analogs by Oxygen Free Radicals.

The above mutagenic ribonucleosides can be chemically modified to obtain a series of analogs with different attached chemical groups on either the base or sugar moieties. Procedures for the chemical modification of these analogs are well known to those schooled in the art of organic chemistry. Selected analogs will be either subject to agents that generate oxygen free radicals (Feig, D., et al., PNAS, 91, GG09–6G13, 1995) or subject to specified chemical modifications to introduce small substituents at multiple positions. The altered nucleotides will be subject to chromatographic separation and the chemical structures will be identified by mass spectroscopy and/or nuclear magnetic resonance. Ribonucleosides will be tested for the induction of mutations in the HIV genome and for causing a progressive loss of viability as outlined below.

2. Mutagenic Ribonucleoside Triphosphate Libraries Using Combinatorial Chemistry.

Mutagenic ribonucleoside triphosphates derivatives of the nucleosides listed above as well as uridine and cytidine triphosphates will be used as core compounds for the synthesis of chemically diverse libraries. Examples of combinatorial type assay formats are described in U.S. Pat. Nos. 5,384,261, 5,143,854, and Chee et al., Science 274:610–614 (1996). Individual analogs will be subjected to reactions that chemically protect the miscoding substituents by standard methods of nucleotide chemistry that are widely practiced in this field. The protected analogs will be subjected to a series of chemical reactions involving but not limited to the following: dehydration, irradiation, oxidation, reduction, alkylations and permutations of the these. Thereafter, the resultant mixture of diverse products comprising a library of greater than five and less than one million chemical species will be subjected to deprotection reactions. The mixture of analogs will be analyzed by measuring the capacity of the mixture to substitute for the complementary nucleoside triphosphate during synthesis by RNA polymerase II or one of the virally encoded RNA replicates using chain elongation reactions. The elongated products will be subjected to polyacrylamide gel electrophoresis. Bands containing the incorporated nucleotides will be isolated and the hydrolyzed to the freebases and the elongated analogs will be identified by mass spectroscopy.

3. Synthesis of 5-bromocytidine, 5-hydroxycytidine and 5-hydroxyuridine.

A 5-hydroxycytidine ($^{5OH}$C) will be synthesized using a variation of the procedure in Visser, D. W., *Synthetic Procedures in Nucleic Acid Chemistry* (Zorbach et al., Eds.), Vol. 1, pp. 428–430, Interscience Publishers, New York (1968).

Deamination of the $^{5OH}$C product, achieved under basic conditions, will provide $^{5OH}$U. In the presence of a large excess of bromine, the corresponding $^{5Br}$C will be obtained. The triphosphate forms of these modified

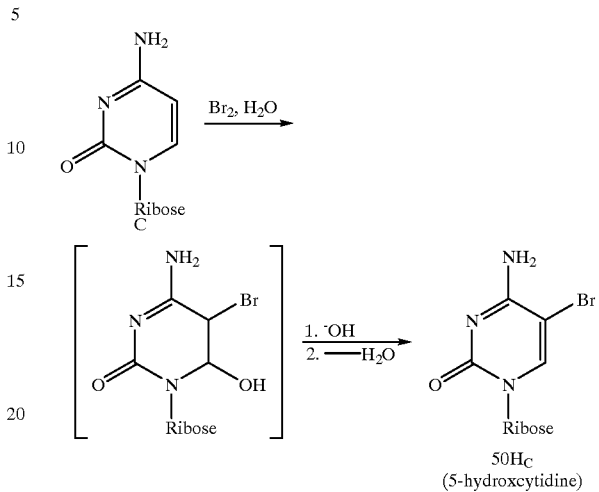

nucleosides, $^{5OH}$CTP, $^{5Br}$CTP and $^{5Br}$UTP, could also be prepared using the corresponding CTP in place of C in the above reaction.

The desired reaction product will be separated from other reaction products using column chromatography followed by recrystallization from hot ethanol.

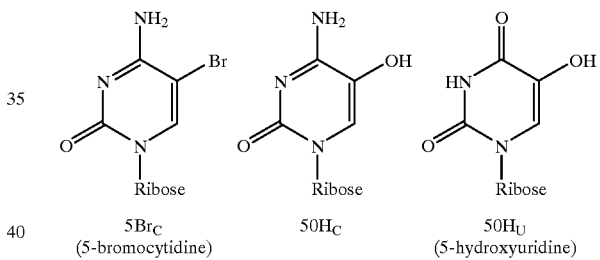

4. Testing of Ribonucleoside Analogs for Toxicity to Human Cells.

Figure 1B:
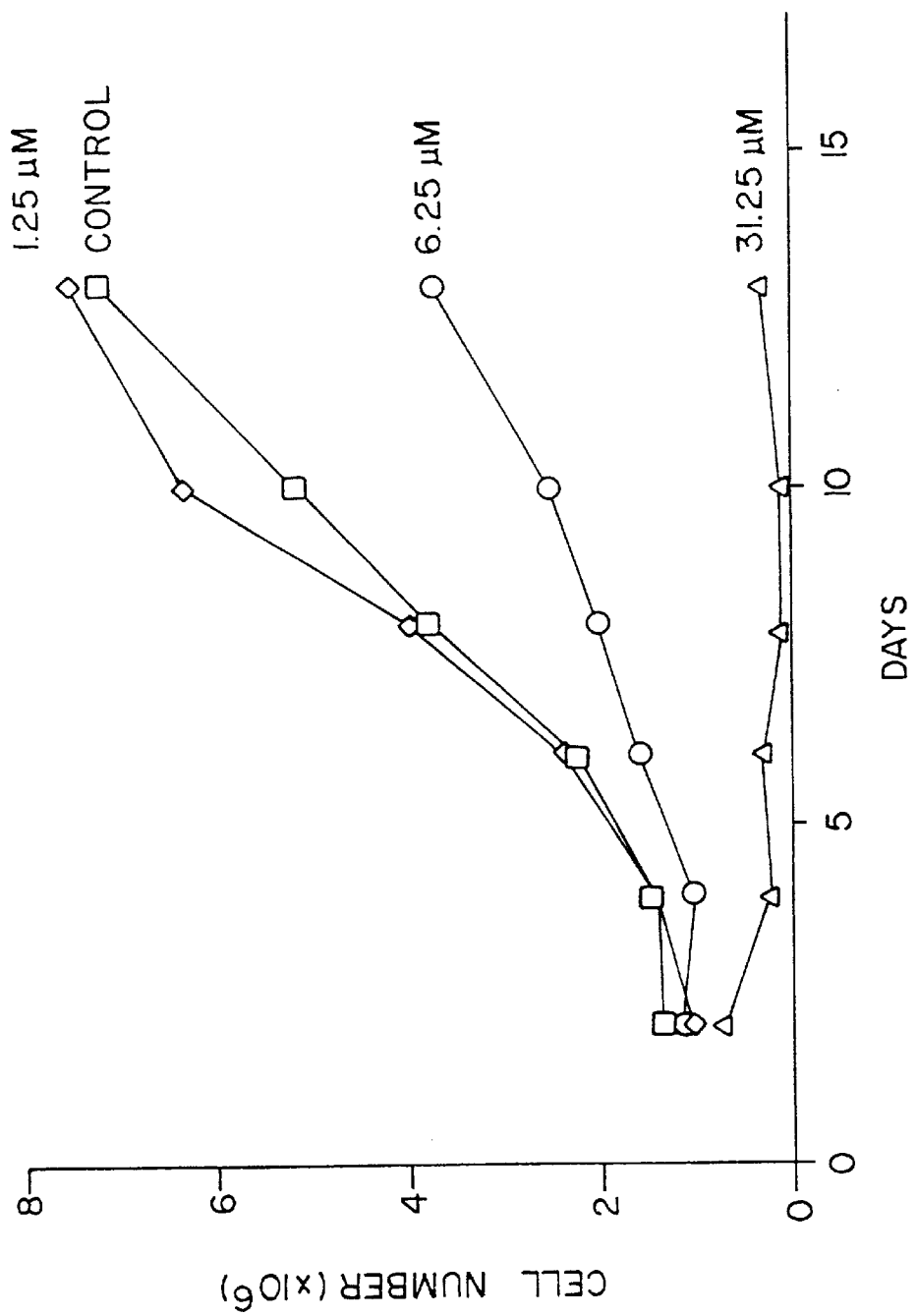

Prior to studying the induction of mutations by culturing HIV infected human cells in the presence of ribonucleoside analogs, we tested for effects on cellular viability. Two ribonucleoside analogs were tested for their effects on viability of CEMx174 cells (human lymphoid transformed cell line; see, e.g., Chen et al., *J. Virology* 71:2705 (1997)) as a function of analog concentration and time in culture. 1×10$^6$ Cells in 2 ml cultures were incubated with serial dilutions of 5-bromocytidine, 5-hydroxyuridine or in the absence of added analogs (control) for up to 14 days. The cultures were split every second day and fresh analog was added at the indicated concentrations. Viability was assessed every second day determining the total number of cells and the percentage of cells that exclude trypan blue (FIGS. 1A and 1B). Appropriate dosages which avoid toxicity can be ascertained from the results.

5. Serial Passage of HIV-1 in the Presence of 5-hydroxyuridine, 5-bromocytidine or Controls.

Figure 2:
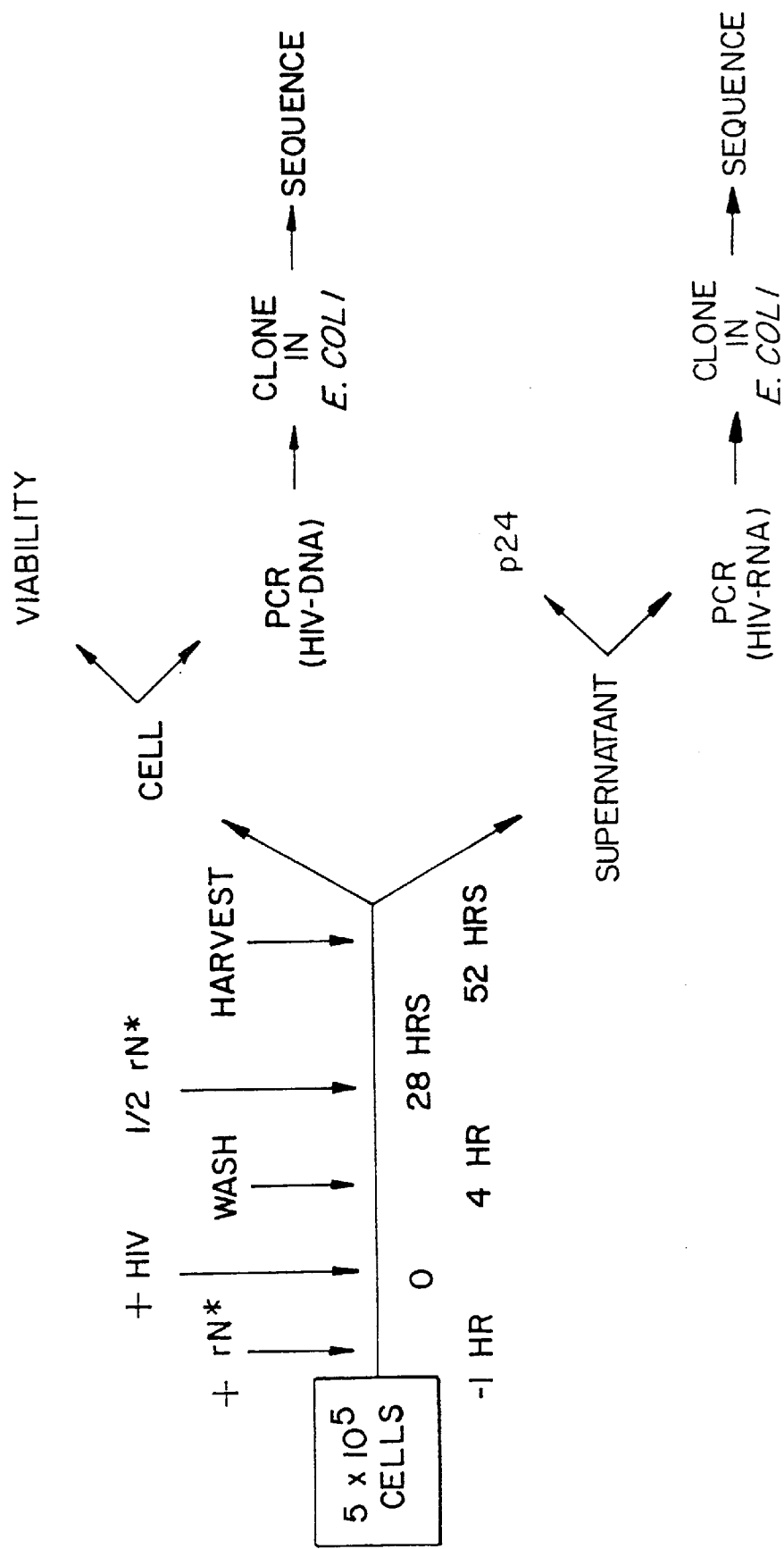
FIG. 2 illustrates the protocol sequence for ribonucleoside (rN*) testing in CEM cells infected with HIV-1 as described in more detail in Example 5, below.
Figure 3:
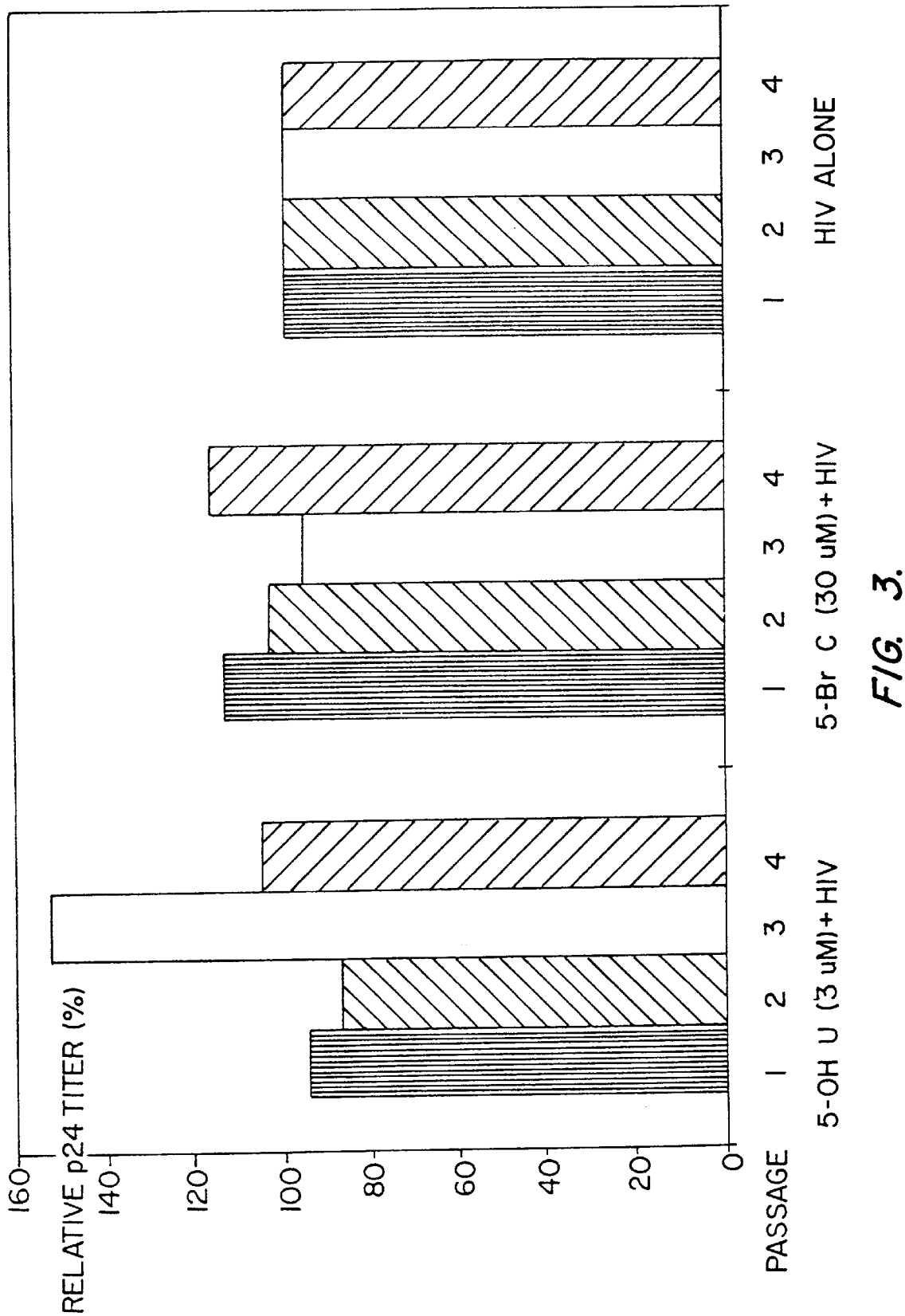
FIG. 3 illustrates the serial passage of HIV-1 in the presence of 5-hydroxyuridine and in the presence of 5-bromocytidine or controls for four passages.

The protocol for measuring the accumulation of mutations in HIV as a function of passage of infected cells in the presence of ribonucleoside analogs is presented in FIG. 2. Stock preparations of HIV containing approximately 10$^6$ infectious units/ml were titered by the syncytium induction assay (Chesebro B. and Wehrly, K., *J. Virol.* 62:3779–3788 (1988)). The virus was added at a multiplicity of 0.012 cells ($2\times10^5$/per ml) that were previously incubated for one hour in the presence or absence of the test ribonucleoside. After four hours at 37° C., the infected cells were washed twice with PBS without $Mg^{2+}$ or $Ca^{2+}$), resuspended in 0.5 ml medium with the indicated concentration of the analog (see FIG. 3). Incubation was carried out in 48-well plates for two days at 37° C. After the second day an additional aliquot of analog corresponding to achieve one half of the initial concentration was added. Cultures were harvested on the fourth day. The cells were separated by centrifugation and one tenth of the supernatant was added to fresh uninfected cells. This procedure was repeated for four cycles and will be continued for thirty cycles unless there is a loss of infectivity of the virions. Virus production during the first four cycles is ascertained by measuring p24 antigen with the Abbott antigen ELISA kit (Abbott Laboratories, Chicago, Ill.) (FIGS. 3 A, B, C).

At the end of thirty passages or one cycle prior to loss of viral infectivity, viral mutagenesis will be determined by cloning and sequencing viral DNA and RNA. A segment of the HIV reverse transcriptase corresponding spanning nucleotides 2193 to 2867 will be amplified from the proviral DNA in cell pellets obtained after 30 passages or from frozen cells obtained immediately preceeding a reproducible dimunition in viral production, DNA will be prepared by quick lysis and a rough estimate of provirus load will be determined by endpoint dilution of the lysate followed by nested PCR using Pfu polymerase (Delwart, E. L. et al., *Science* 262:1257–1261 (1993)). The number of clones that can be derived from each PCR reaction without the likelihood of resampling will then be estimated (Liu, S.-L. et al., *Science* 273:415–416 (1996)). Thirty cycles of PCR will first be carried out with outer primers, followed by dilution into fresh reaction mixture containing inner primers and an additional 20 cycles of amplification. The inner primers will contain 5' terminal sequences that are not complementary to HIV and encode restriction sites for cloning into M13mp2 DNA. After restriction enzyme digestion, the fragments will be ligated into M13mp2 DNA previously digested with the same enzymes. The nucleotide sequence of the HIV inserts will be determined by sequencing the single-stranded M13 plasmids. A similar procedure will be carried out starting with viral RNA in the supernatant fraction. It is advantageous to analyze several analogs simultaneously. For each analog and the control, we will sequence approximately 20 clones. The predicted alteration in the mutation spectrum of analog-exposed virus compared to controls would establish the introduction of mutations by the analog.

6. HEPATITIS C VIRUS/DENGUE FEVER VIRUS

Hepatitis C virus (HCV) is a major human pathogen and a suitable target for the analogs of this invention. HCV is a positive stranded RNA virus of the Flaviviridae family. HCV is a difficult virus to grow in vitro, though some success has been reported in lymphoblastoid and hepatocyte cell lines. As a proxy for testing RNA analogs against HCV, such analogs can be tested against another member of Flaviviridae, dengue virus, that is responsible for dengue fever and its hemorrhagic variant. Dengue viruses grow in a variety of primary and continuous cell cultures. Cells of human (BSC-1), monkey (LLC-MK2, Vero, primary kidney monkey), hamster (BKH-21), and mosquito origin are most susceptible. Yields of up to 7 dex and plaque formation are obtained under appropriate conditions.

One of the preferred RNA analogs can be used for the in vitro mutagenic analysis. At the end of a suitable number of passages or one cycle prior to loss of viral infectivity, viral mutagenesis can be determined by cloning and sequencing of viral RNA. Analysis of incorporation of viral mutagenesis by RNA analogs can be determined in a manner similar to that described for HIV after selection of a segment of the viral genome for analysis.

What is claimed is:

1. A method of increasing the mutation rate of a virus, comprising administering an RNA nucleoside analog to a virally infected cell, wherein the analog is incorporated by a polymerase into an RNA copy of a genomic nucleic acid encoding the virus, said analog replacing a first natural occurring nucleotide having a first complementary nucleotide wherein said analog complements a second nucleotide which is other than the first nucleotide, thereby inducing the virus to mutate.

2. The method of claim 1, wherein the RNA nucleoside analog replaces uracil.

3. The method of claim 1, wherein the RNA nucleoside analog replaces adenine.

4. The method of claim 1, wherein the RNA nucleoside analog replaces cytidine.

5. The method of claim 1, wherein the RNA nucleoside analog replaces guanine.

6. The method of claim 1, wherein the RNA nucleoside analog is incorporated by the polymerase into the RNA copy of the genomic nucleic acid with an efficiency at least about 0.1% that of a naturally occurring complementary nucleic acid.

7. The method of claim 1, wherein the method further includes the proviso that the RNA nucleoside analog is not ribavirin or a 5-halo analog of 1-β-D-ribofuranosylimidazole-4-carboxamide.

8. The method of claim 1 wherein the RNA analog is a non-chain terminating analog.

9. The method of claim 1, wherein the method further includes the proviso that if the virus is HIV, then the RNA nucleoside analog is not HEPT or a 2',5'-bis-O-silylated-3'-spiro-substituted (TSAO) adenine, hypoxanthine, $N^1$-alkyl-hypoxanthine, or xanthine or a nucleoside analog that is incorporated and extended at high efficiency by reverse transcriptase of HIV.

10. The method of claim 1, wherein the nucleoside analog is selected from the group consisting of $N^4$-aminocytidine, $N^1$-methyl-$N^4$-aminocytidine, 3,$N^4$-ethenocytidine, 3-methylcytidine, 5-hydroxycytidine, $N^4$-dimethylcytidine, 5-(2-hydroxyethyl)-cytidine, 5-chlorocytidine, 5-bromocytidine, $N^4$-methyl-$N^4$-aminocytidine, 5-aminocytidine, 5-nitrosocytidine, 5-(hydroxyalkyl)-cytidine, 5-(thioalkyl)-cytidine and cytidine glycol, 5-hydroxyuridine, 3-hydroxyethyluridine, 3-methyluridine, $O^2$-methyluridine, $O^2$-ethyluridine, 5-aminouridine, $O^4$-methyluridine, $O^4$-ethyluridine, $O^4$-isobutyluridine, $O^4$-alkyluridine, 5-nitrosouridine, 5-(hydroxyalkyl)-uridine, and 5-(thioalkyl)-uridine, 1,$N^6$-ethenoadenosine, 3-methyladenosine, and $N^6$-methyladenosine, 8-hydroxyguanosine, $O^6$-methylguanosine, $O^6$-ethylguanosine, $O^6$-isopropylguanosine, 3,$N^2$-ethenoguanosine, $0^6$-alkylguanosine, 8-oxo-guanosine, 2,$N^3$-ethenoguanosine, and 8-aminoguanosine.

11. The method of claim 1, wherein the virus is a retrovirus.

12. The method of claim 1, wherein the polymerase is a human polymerase II.

13. The method of claim 1, wherein the cell is in cell culture.

14. The method of claim 1, wherein the cell is in an animal.

15. The method of claim 1, wherein increasing the mutation rate of the virus produces a progressive loss of viability of the virus.

16. The method of claim 1, comprising administration of more than one species of RNA nucleoside analog to the virally infected cell.

17. The method of claim 1, wherein the virus is an RNA virus selected from the group consisting of hepatitis C, coronavirus, influenza, respiratory syncytial virus and dengue fever.

18. The method of claim 1, wherein the RNA nucleoside analog is an enantio-specific nucleoside analog.

19. A retroviral particle comprising viral genomic RNA, wherein the viral genomic RNA comprises an RNA nucleoside analog.

20. The retroviral particle of claim 19, wherein the particle is an HIV particle.

21. The retroviral particle of claim 19, wherein the nucleoside analog is selected from the group consisting of $N^4$-aminocytidine, $N^1$-methyl-$N^4$-aminocytidine, 3,$N^4$-ethenocytidine, 3-methylcytidine, 5-hydroxycytidine, $N^4$-dimethylcytidine, 5-(2-hydroxyethyl)-cytidine, 5-chlorocytidine, 5-bromocytidine, $N^4$-methyl-$N^4$-aminocytidine, 5-aminocytidine, 5-nitrosocytidine, 5-(hydroxyalkyl)-cytidine, 5-(thioalkyl)-cytidine and cytidine glycol, 5-hydroxyuridine, 3-hydroxyethyluridine, 3-methyluridine, $O^2$-methyluridine, $O^2$-ethyluridine, 5-aminouridine, $O^4$-methyluridine, $O^4$-ethyluridine, $O^4$-isobutyluridine, $O^4$-alkyluridine, 5-nitrosouridine, 5-(hydroxyalkyl)-uridine, and 5-(thioalkyl)-uridine, 1,$N^6$-ethenoadenosine, 3-methyladenosine, and $N^6$-methyladenosine, 8-hydroxyguanosine, $O^6$-methylguanosine, $O^6$-ethylguanosine, $O^6$-isopropylguanosine, 3,$N^2$-ethenoguanosine, $0^6$-alkylguanosine, 8-oxo-guanosine, 2,$N^3$-ethenoguanosine, and 8-aminoguanosine.

22. A method of increasing the mutation rate of a virus, comprising administering a free base selected from the group comprising adenine, cytosine, guanine, uracil and thymine to a virally infected cell, wherein the base is incorporated by a polymerase into an RNA or DNA copy of a genomic nucleic acid encoding the virus, said base replacing a first natural occurring nucleotide having a first complementary nucleotide wherein said base complements a second nucleotide which is other than the first nucleotide, thereby inducing the virus to mutate.

* * * * *

UNITED STATES PATENT AND TRADEMARK OFFICE
CERTIFICATE OF CORRECTION

PATENT NO.   : 6,063,628
DATED        : May 16, 2000
INVENTORS    : Lawrence A. Loeb, James I. Mullins It is certified that there is an omission in the above-identified patent and that said Letters Patent is hereby corrected as shown below:

Column 1, line 8:
Please insert the following funding statement:

--This invention was made with government support under Grant Number NCI 01G-R35-CA-39903 awarded by the National Institutes of Health. The Government has certain rights in the invention.--

Signed and Sealed this

Seventeenth Day of April, 2001

*Attest:*

NICHOLAS P. GODICI

*Attesting Officer*     *Acting Director of the United States Patent and Trademark Office*